(12) United States Patent
Kritzman

(10) Patent No.: US 10,285,405 B2
(45) Date of Patent: *May 14, 2019

(54) OIL CARRYING PARTICULATE MATTER AND USES THEREOF

(71) Applicant: Nobactra Israel Ltd., Sde Warburg (IL)

(72) Inventor: Giora Kritzman, Raanana (IL)

(73) Assignee: Nobactra Israel Ltd., Sde Warburg (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/441,827

(22) PCT Filed: Apr. 10, 2014

(86) PCT No.: PCT/IL2014/050346
§ 371 (c)(1),
(2) Date: May 8, 2015

(87) PCT Pub. No.: WO2014/170893
PCT Pub. Date: Oct. 23, 2014

(65) Prior Publication Data
US 2015/0289520 A1 Oct. 15, 2015

(30) Foreign Application Priority Data
Apr. 18, 2013 (IL) .......................................... 225825

(51) Int. Cl.
| | |
|---|---|
| *A01N 25/04* | (2006.01) |
| *A01N 63/00* | (2006.01) |
| *A01N 65/00* | (2009.01) |
| *A01N 65/22* | (2009.01) |
| *A01N 65/08* | (2009.01) |
| *B65D 75/36* | (2006.01) |
| *B65D 81/32* | (2006.01) |
| *A01N 25/08* | (2006.01) |
| *C12R 1/38* | (2006.01) |

(52) U.S. Cl.
CPC ............. *A01N 63/00* (2013.01); *A01N 25/04* (2013.01); *A01N 25/08* (2013.01); *A01N 65/00* (2013.01); *A01N 65/08* (2013.01); *A01N 65/22* (2013.01); *B65D 75/367* (2013.01); *B65D 81/3261* (2013.01); *C12R 1/38* (2013.01)

(58) Field of Classification Search
None
See application file for complete search history.

(56) References Cited

U.S. PATENT DOCUMENTS

| | | | |
|---|---|---|---|
| 6,099,864 A * | 8/2000 | Morrison | A61K 9/1277 264/4.1 |
| 6,156,560 A | 12/2000 | Chun | |
| 6,231,865 B1 | 5/2001 | Hsu et al. | |
| 6,495,133 B1 | 12/2002 | Xue | |
| 7,351,417 B2 * | 4/2008 | Barrow | A61K 8/042 424/401 |
| 7,485,451 B2 | 2/2009 | VanderGheynst et al. | |
| 8,299,162 B2 * | 10/2012 | Mateu | A61K 8/042 424/401 |
| 9,380,788 B2 | 7/2016 | Kritzman | |
| 2005/0214337 A1 | 9/2005 | McGee et al. | |
| 2006/0153886 A1 * | 7/2006 | Leigh | A61K 8/0279 424/401 |
| 2007/0298000 A1 * | 12/2007 | Grune | A61K 8/27 424/59 |
| 2011/0014596 A1 | 1/2011 | Kurenov et al. | |
| 2011/0028500 A1 | 2/2011 | Su et al. | |
| 2011/0033436 A1 | 2/2011 | Chen et al. | |
| 2011/0082040 A1 | 4/2011 | Trevino et al. | |
| 2011/0250249 A1 * | 10/2011 | Mateu | A61K 8/042 424/401 |
| 2012/0083412 A1 | 4/2012 | Trevino et al. | |

FOREIGN PATENT DOCUMENTS

| | | |
|---|---|---|
| GB | 2376887 A | 12/2002 |
| GB | 2449876 A | 12/2008 |
| IN | 3603/CHE/2010 | 12/2010 |
| JP | 2-221208 A | 9/1990 |
| JP | 7-109209 A | 4/1995 |
| JP | 2002-521406 A | 7/2002 |
| JP | 2009-526644 A | 7/2009 |
| JP | 2010-150178 A | 7/2010 |

(Continued)

OTHER PUBLICATIONS

Kleitman et al., "Characterization of a *Clavibacter michiganensis* Subsp. Michiganensis Population in Israel", European Journal of Plant Pathology, vol. 121, 2008, pp. 463-475.

Lanteigne et al., "Production of DAPG and HCN by *Pseudomonas* sp. LBUM300 Contributes to the Biological Control of Bacterial Canker of Tomato", Phytopathology, vol. 102, No. 10, 2012, pp. 967-973.

Pouvova et al., "Effectivity of Plant Essential Oils Against Clavibacter Michiganensis, In Vitro", Zemdirbyste-Agriculture, vol. 95, No. 3, 2008, pp. 440-446.

(Continued)

*Primary Examiner* — Johann R Richter
*Assistant Examiner* — Danielle Sullivan
(74) *Attorney, Agent, or Firm* — Vorys, Sater, Seymour and Pease LLP

(57) ABSTRACT

The present disclosure provides a particulate matter comprising particles carrying an essentially dry combination of components comprising at least one natural oil and at least one surfactant, the components being selected such that upon contact with water, oil in water emulsion is formed. In particular, the emulsion formed is a stable emulsion, with stability of at least several hours, as observed by the lack of phase separation during that time.

17 Claims, No Drawings

(56) References Cited

FOREIGN PATENT DOCUMENTS

| | | | |
|---|---|---|---|
| RU | 2324352 | C2 | 5/2008 |
| RU | 2464210 | C2 | 10/2012 |
| WO | 00/05964 | A1 | 2/2000 |
| WO | 2004/034791 | A1 | 4/2004 |
| WO | 2004/060231 | A1 | 7/2004 |
| WO | 2004/073689 | A1 | 9/2004 |
| WO | 2004/075872 | A1 | 9/2004 |
| WO | 2006/029718 | A1 | 3/2006 |
| WO | 2006/057974 | A1 * | 6/2006 |
| WO | 2006/060213 | A2 | 6/2006 |
| WO | 2007/094000 | A2 | 8/2007 |
| WO | 2008/132719 | A2 | 11/2008 |
| WO | 2010/011740 | A2 | 1/2010 |
| WO | 2013/127790 | A2 | 9/2013 |
| WO | 2016/005974 | A1 | 1/2016 |

OTHER PUBLICATIONS

Ślusarski, Czesiaw, "Attempts at Biological Control of *Clavibacter michiganensis* Subsp. Michiganensis on Rockwool-Grown Greenhouse Tomatoes", Vegetable Crops Research Bulletin, vol. 69, 2008, pp. 125-134.

Talibi et al., "Antibacterial Activity of Moroccan Plants Extracts Against *Clavibacter michiganensis* Subsp. Michiganensis, the Causal Agent of Tomatoes Bacterial Canker", Journal of Medicinal Plants Research, vol. 5, No. 17, Sep. 9, 2011, pp. 4332-4338.

Olanya, et al., "Efficacy of Essential Oils and Biopesticides on Phytophthora Infestans Suppression in Laboratory and Growth Chamber Studies", Biocontrol Science and Technology, vol. 16, No. 9, 2009, pp. 901-917.

* cited by examiner

OIL CARRYING PARTICULATE MATTER AND USES THEREOF

CROSS REFERENCE TO RELATED APPLICATIONS

This application is a U.S. national stage application of PCT/IL2014/050346, filed internationally on Apr. 10, 2014, which is incorporated herein by reference in its entirety and which claims priority to Israeli Patent Application No. 225825, filed Apr. 18, 2013.

TECHNOLOGICAL FIELD

The present disclosure concerns oil particulate products, for use, inter alia, in agriculture.

PRIOR ART

References considered to be relevant as background to the presently disclosed subject matter are listed below:
Japanese patent application publication No. JP2010150178;
International patent application publication No. WO04034791;
Acknowledgement of the above references herein is not to be inferred as meaning that these are in any way relevant to the patentability of the presently disclosed subject matter.

BACKGROUND

The absorption of oil on particles to obtain oil powder has been described, for example in Japanese patent application publication No. JP2010150178. According to this publication, there is provided an antibacterial functional powder composed of porous calcium carbonate and an essential oil.

In addition, International patent application publication No. WO04034791 describes a controlled release composition comprising an essential oil having pesticidal and/or fungicidal properties, a supporting material therefor and means for controlling the release of the essential oil from the supporting material. The composition is in the form of a free flowing powder. The supporting material is one that may be a material, e.g. a powder material, that is capable of absorbing the essential oil to an extent that the resultant mixture is in the form of a free-flowing powder, such as clays and silicas, celites; zeolites. The means for controlling the release of the essential oil from the supporting material is a high molecular weight, low melting wax or solid that is mixed with the support material.

GENERAL DESCRIPTION

The present disclosure provides, in accordance with its broadest aspect, particulate matter comprising particles carrying an essentially dry combination of components comprising at least one natural oil and at least one surfactant, the components being selected such that upon contact with water, an oil in water emulsion is formed. Preferably, the oil in water emulsion is a stable emulsion with no phase separation for at least 24 hours from its preparation.

The present disclosure also provides a composition comprising particulate matter as defined herein. The composition comprises, in addition to the particulate matter, any adjuvant, additive, excipient etc., suitable and selected in accordance with the intended application. For example, the additional component may be one required to facilitate the use of the particulate matter in agriculture.

The particulate matter may comprise a single population of particles having one or more natural (e.g. essential) oils carried on the same particles, or a combination of populations, namely, one population of particles carried one type or one group of oils and at least one other population carrying another type or another group of oils, both types of population being as further discussed below.

In some embodiments, the at least one natural oil is one being characterized with anti-microbial activity.

Therefore, the present disclosure also provides the use of the particulate matter as defined for the preparation of an anti-microbial emulsion.

Further, the present disclosure provides a method of producing an anti-microbial emulsion comprising mixing the particulate matter with an aqueous solution to form said anti-bacterial emulsion.

Finally, the present disclosure provides a method of treating a plant, the method comprising, mixing the particulate matter with an aqueous solution to form an emulsion; and applying said emulsion onto at least part of the plant or to soil surrounding the plant.

When requiring anti-microbial activity, the emulsion may be combined or used in combination with other anti-microbial agents as known in the art.

DETAILED DESCRIPTION OF EMBODIMENTS

The present invention is based on the development of particulate material comprising a particulate carrier having absorbed thereon functional oils such that upon contact with water or water based solutions, a stable emulsion is formed.

Thus, in its broadest aspect, the present disclosure provides particulate matter comprising particles carrying an essentially dry combination of components, the combination comprising at least one oil and at least one surfactant, and the components being selected such that upon contact with water, oil in water emulsion is formed.

In the context of the present disclosure, the term "particulate matter" is used to denote a substance in the form of plurality of particle. The particles may be in any particulate form, including, without limited thereto, from finely rounded beads to amorphous structures. The particulate matter also includes any form of a powder.

In some embodiments, the particulate matter comprise silica dioxide ($SiO_2$, referred to herein as silica). The silica may be naturally occurring silica particles such as bentonite clay beads, as well as synthetic silica beads, as known in the art.

In some embodiments, the particulate matter comprises synthetic silica. There is a variety of synthetic silica that may be used in the context of the present disclosure. For example, the particulate matter may comprise precipitated synthetic amorphous silica beads, such as the commercially available products Tixosil and Aerosil 200.

In some other embodiments, the particulate matter comprises synthetic or nature derived beads with a capacity to absorb natural oils. Such beads may include, without being limited thereto Latex beads; calcium carbonate sorbent particle; cellulose beads; polystyrene adsorbents beads e.g. Amberlite® XAD®-2 which is a hydrophobic crosslinked polystyrene copolymer absorbent resin; charcoal; Sepharose™ beads; emulsan-alginate beads; chitosan beads; sodium alginate; styrene-maleic acid copolymer beads and styrene-divinylbenzene beads; cellulose paper beads.

To allow good distribution of the final emulsion and in accordance with some embodiments the particulate matter (particles) has a size distribution in the range of 10-25 µm, at times 15 to 22 µm.

The particulate matter may also be characterized, without being limited thereto, by its surface area, in some embodiments, the particulate matter has a specific surface area ($N_2$) in the range of 400-550 $m^2/g$, at times, in average 500 $m^2/g$.

In some further embodiments, particulate matter may also be characterized, without being limited thereto, by its DBP absorption. The DBP absorption (DOA absorption) is commonly used numerical value used to indicate absorption capacity of fillers and in the present disclosure indicates the oil capacity of the particulate matter. In some embodiments, the DBP is in the range of 250-350 ml/100 gram particles, at times, 280-320 ml/100 gram.

The first component comprises the particulate matter that holds one or a combination of natural oils. In the context of the present disclosure it is to be understood that "natural oil" encompasses any organic oil obtained from nature.

The natural oil is preferably oil derived from a plant. In some embodiments, the natural oils are essential oils. Essential oils are preferably those known to exhibit antimicrobial (e.g. antibacterial) properties. In this context, when referring to anti-microbial properties of the essential oils, it is to be understood as being effective against any microbial pathogen, as further discussed below.

There are a variety of essential oils. Without being limited thereto, essential oils to be used in accordance with the present disclosure, may be those derived from the plants *Origanum vulgare* and *Origanum* spp., (e.g. Oregano), *Mentha* spp. (mint), *Thymus* spp. (Thyme), *Myrtus* spp., *Ocimun* spp. (e.g. *Ocimun basilicum*, also known as Basil), *Lavandula* spp. (e.g. Lavender), *Micromeria* spp., *Coriandum* spp. (e.g. Coriander/Parsley), *Aloysia* spp., *Melissa* spp., *Salvia* spp., *Petoselinum* spp., *Rosmarinus* spp. (e.g. Rosemary), *Prunella* spp., *Cuminum* spp (e.g. Cumin).

In some other embodiments, the natural oils are plant derived oils that are used as carbon source, e.g. as food/nutrient for the antagonistic microorganisms. These are referred to herein the term "carbon-base oil" or "carbon-rich nutrient oil". In some embodiments, the carbon-base oils are vegetable oils. Without being limited thereto, the carbon-base oil is selected from the group consisting of Sesame oil, Olive oil, Peanut oil, Cottonseed oil, Soybean oil, Palm oil, sunflower oil, safflower oil, canola oil, castor oil, coconut oil, groundnut oil.

In some preferred embodiments, the natural oil is a combination of at least one essential oil and at least one carbon-base oil. As such, when referring to natural oil it is to be understood as also encompassing essential oil(s) and carbon-base oil(s). When in combination, the ratio between the at least one essential oil and at least one carbon-base oil is in the range of 60:40 and 100:0, at times the range is about 80:20.

When a combination of oils is used it is to be understood that they may be absorbed onto the particulate matter together, i.e. the same particulate matter holds more than one type of oil. In some embodiments, each oil type is held separately on particulate matter such that different types of particulate matter are formed, each being characterized by the type of oil it is holding.

Thus, when referring to particular matter providing essential oil (e.g. Oregano) and carbon base oil (e.g. Sesame) at a ratio of 80:20 it is to be understood as either a single population of particulate matter onto which the two types of oil have been absorbed at the recited ration or to a mixture of two populations of particulate matter, 80% carrying only essential oil such as Oregano and 20% carrying carbon base oil, such as Sesame oil. Irrespective of the oil type, the particulate matter between 20% to 50% w/w of its total weight it provided by the oil loaded thereon.

In some embodiments, the natural oil comprises at least Oregano oil in combination with at least one carbon-base oil. The Oregano oil is combined, at times, with at least Sesame oil.

The amount of natural oils held by (absorbed by) the particles may vary, depending on the type(s) of natural oil used, the amount at loading, the type of particles used, the conditions of loading the natural oil onto the particulate matter, the surfactants and solvents used for loading etc.

When referring to loading of oil onto the particles, it is to be understood as meaning any form of association between the oil and the particles (e.g. silica particles). Without being limited thereto, the oil is held by the particles by absorption onto and/or into the particles. The association between the particles and the oil is reversible, namely, under suitable conditions, such as when brought into contact with water, the oil is released from the particles to form an emulsion.

To this end, the present disclosure also provides a stable emulsion provided by said particulate matter, comprising the particles, at least one natural oil and at least one surfactant.

In some embodiments, the particles hold between 20% to 50% w/w natural oil out of the total weight of the particulate matter (after loading). This is determined by conventional techniques such as HPLC or GC chromatography, as also exemplified below. In some other embodiments, the particles hold about 30% w/w natural oil at times, between 25-35%, at times between 28% to 32%, at times, around 30%.

The particulate matter also comprises at least one surfactant. As appreciated, a surfactant is a compound that lowers the surface tension of a liquid and as such, the interfacial tension between two liquids to allow the formation of, e.g. an emulsion. It has been found by the inventors, as also shown in the following non-limiting examples, that the surfactant is essential in order to provide a stable emulsion, once the dry particulate matter is brought into contact with water.

The surfactant may be of any kind known in the art as safe for use (e.g. non-toxic to plants or animals) in agriculture.

In some embodiments, the surfactant is a non-ionic surfactant, particularly those known to be suitable for agricultural applications.

A non-limiting list of possible non-ionic surfactants to be used in accordance with the present disclosure includes Polyethylene glycol sorbitan trioleates (Tween) such as Polyoxyethylenesorbitan Trioleate (Tween 85), Polyoxyethylenesorbitan Tristearate (Tween 65), sorbitan fatty acid esters, such as Sorbitan monopalmitate (Span 40)), Alcohol alkoxylate (BS1000).

In some other embodiments, the surfactant comprises a salt of a fatty acid. The salt may comprise an alkaline such as potassium, calcium, sodium salts, as well as an ammonium salt.

In some embodiments, the salt of a fatty acid comprises potassium salts of fatty acids (also known as soap salts), which are typically uses as insecticides, herbicides, fungicides, and/or algaecides (these are at times considered non-ionic surfactants). In some embodiments, potassium salts of fatty acids may be obtained by adding potassium hydroxide to natural fatty acids such as those found in animal fats and in plant oils. Fatty acids may be extracted from vegetative sources such as olives, cotton seeds, soya beans, peanuts, sun flowers, coconuts Palm, Rapeseed, Sesame, Amaranth, Corn, Jatropha.

The fatty acid forming the surfactant may also be a synthetic fatty acid as well as a semi-synthetic (e.g. a natural fatty acid that underwent a modification).

In accordance with some embodiments, the surfactant is one being recognized or is labeled as having an insecticide and/or fungicide activity. Without being limited thereto, pesticidal and/or fungicidal surfactants may include the commercial products Zohar PT-50 and Zohar LQ-215, both produced by Zohar Dalia, Israel.

In one particular embodiment, the surfactant is selected from Zohar PT-50 and Zohar LQ-215.

The compositions of these surfactants are available from Zohar Dalia. For instance, Zohar PT-50 is known to have the following composition:

embodiments, the water content in the particulate matter is within the range of 1% to 7% (w/w)).

The particulate matter may also contain some trace amounts of organic solvent(s). As will be further discussed below, the solvent is required for the preparation of the particulate matter and some residual amounts may remain in the final particulate matter. In some embodiments, the particulate matter comprises no more than 5%, 4%, 3% or even 2% w/w organic solvent. The solvent is typically an organic volatile polar solvent, such as, without being limited thereto, a solvent selected from the group consisting of acetone, isopropyl alcohol, acetonitrile, ethanol and methanol.

In one particular embodiment, the solvent is ethanol.

The particulate matter is unique in its capability of forming a stable emulsion, once the particulate matter is brought into contact with water.

| Vegetable oils | | | | | | | |
|---|---|---|---|---|---|---|---|
| | | | Polyunsaturated fatty acids | | | | |
| Type | Saturated fatty acids | Mono-unsaturated fatty acids | Total poly | linolenic acid ($\omega$-3) | Linoleic acid ($\omega$-6) | Oleic acid ($\omega$-9) | Smoke point |
| Not hydrogenated | | | | | | | |
| Canola (rapeseed) | 7.365 | 63.276 | 28.14 | 9-11 | 19-21 | — | 204° C. |
| Coconut | 91.00 | 6.000 | 3.00 | — | 2 | 6 | 177° C. |
| Corn | 12.948 | 27.576 | 54.67 | 1 | 58 | 28 | 232° C. |
| Cottonseed | 25.900 | 17.800 | 51.90 | 1 | 54 | 19 | 216° C. |
| Flaxseed/Linseed (European) | 6-9 | 10-22 | 68-89 | 56-71 | 12-18 | 10-22 | 107° C. |
| Olive | 14.00 | 72.00 | 14.00 | <1.5 | 9-20 | — | 193° C. |
| Palm | 49.300 | 37.000 | 9.30 | — | 10 | 40 | 235° C. |
| Peanut | 16.900 | 46.200 | 32.00 | — | 32 | 48 | 225° C. |
| Safflower (>70% linoleic) | 8.00 | 15.00 | 75.00 | — | — | — | 210° C. |
| Safflower (high oleic) | 7.541 | 75.221 | 12.82 | — | — | — | 210° C. |
| Soybean | 15.650 | 22.783 | 57.74 | 7 | 50 | 24 | 238° C. |
| Sunflower (<60% linoleic) | 10.100 | 45.400 | 40.10 | 0.200 | 39.800 | 45.300 | 227° C. |
| Sunflower (>70% oleic) | 9.859 | 83.689 | 3.79 | — | — | — | 227° C. |
| Fully hydrogenated | | | | | | | |
| Cottonseed (hydrog.) | 93.600 | 1.529 | .587 | | .287 | | |
| Palm (hydrogenated) | 47.500 | 40.600 | 7.50 | | | | |
| Soybean (hydrogenated) | 21.100 | 73.700 | .400 | .096 | | | |

Values as percent (%) by weight of total fat.

The results provided herein show that a salt of a fatty acid as disclosed herein had some advantage in terms of stability and/or emulsification properties of the powder, and antimicrobial activity, over other known surfactants, such as the commercially known Tween 20 or Tween 80.

The amount of the surfactant may vary. In some embodiments, the particulate matter comprises between 5% to 10% w/w of one or a combination of surfactants.

The particulate matter is in an essentially dry form. When referring to "essential dry" it is to be understood that the particulate matter is either completely dry (as determined by conventional methods) or contain low amounts of water, i.e. no more than 10% (w/w). In some other or additional In the context of the present disclosure, when referring to a stable emulsion it is to be understood as referring to dispersion of oil (the dispersed phase) in water (the dispersion medium) for a period of at least 1 hour, at times, at least 2, 3, 4, 5 or even 10 hours following the formation of the emulsion. In other words, the stability is determined by the lack of visible separation into an oil phase and a water phase.

Without being bound by theory, it is the inventor's position that the incorporation of a surfactant in the particulate matter contributes to the stability of the emulsion formed. This is also evident from the non-limiting examples provided hereinbelow, where the use of potassium salts of fatty acids showed an advantage in terms of stability and safety over other types of commercially available surfactants.

To form the emulsion, the particulate matter is mixed with water. The amount of water depends on the amount of particulate matter. In some embodiments, for each gram of particulate matter (30% of which is oil), water is added to provide a one liter emulsion. As such, in a 1 liter emulsion, 0.1 gr particulate matter provides an oil concentration of 0.03% v/v). In some embodiments, the percentage of oil in the final emulsion is in the range of 0.03% and 2% v/v.

In some embodiments, the mixing of the particulate matter with water provides an emulsion with a droplet size in the range of between 1 to 20 μm and in some embodiments in the range between 3 to 10 μm.

In some embodiments, the emulsion is an anti-microbial emulsion.

The particulate matter may be used as is or in combination with other ingredients, to form a composition comprising the particulate matter. The additional ingredients may depend on the intended use of the particulate matter. For example, the particulate matter may be combined with other dry powders including antimicrobial activity, additional dry surfactants.

In some embodiments, the composition may comprise a single type (population) of particulate matter. In some other embodiments, the particulate matter may comprise a combination of two or more populations of particulate matter, each population being different from the other at least in the type of essential oil absorbed therein. The composition is a dry composition comprising dry particulate matter.

The present disclosure also provides a method of producing an anti-microbial emulsion comprising mixing the particulate matter or a composition comprising the particulate matter with an aqueous solution to form the emulsion, in particular, a stable emulsion. The thus formed emulsion is characterized, inter alia, with formation of droplets, with an average droplet size in the range of 3 to 10 m.

The present disclosure also provides a method of treating a plant, the method comprises mixing particulate matter disclosed herein with an aqueous solution to form an emulsion and applying said emulsion onto at least part of the plant or to soil surrounding the plant.

The application of the emulsion may be by any means known in agriculture, including, without being limited thereto, spraying the plant, irrigation.

In yet some other embodiments, the treatment may include application onto the plant tubers, such as spraying of potato tubers (at times referred to as low spraying of tubers).

The emulsion may be applied to a plant in combination with other active principles, such as one or more antimicrobial agents. To this end, the particulate matter is mixed with at least one antimicrobial agent prior to, concomitant with or subsequent to the formation of the emulsion.

The final emulsion (with or without additional active principles) may be applied to the plant once, twice or more times. When more than one dose is applied, the doses may be provided with time intervals between applications of between one day interval to more than one days (two, three and more days interval). The different doses may be the same or different.

DESCRIPTION OF NON-LIMITING EXAMPLES

Example 1: Verifying Anti-Bacterial Effect of Essential Oils

Materials and Methods

To verify the anti-bacterial effect of essential oil, the following assay was conducted.

Oil:
Oregano oil with the following particulars: country of origin: Bulgaria; plant parts: flowering plant; cultivation method: certified organics, method of extraction: steam distilled.

Bacterial Strains:
*Escherichia coli, Staphylococcus aureus, Salmonella, Clavibacter* and *Xanthomonas campestris* were obtained from the collection of Prof. G. Kritzman Israel.

Disc Diffusion Method:
Bacteria were grown in nutrient broth test tubes at 27° C. for 24 hrs. The paper discs were sterilized by autoclave in preparation for the disc diffusion method. Each bacteria (100 l), was placed on Nutrient agar (NA) plates and allowed to dry for 3-5 minutes. The paper discs were saturated in 100% concentration of the oregano essential oil (20 ul), and then placed onto each NA plate freshly coated with bacteria. The positive control used was 3% $H_2O_2$ solution and the negative control was DI water. The plates were incubated at 27° C. for 48 hours. The zone of inhibition was measured by standard ruler.

Results

The anti-bacterial effect of the commercial organic oils on bacteria is summarized in Table 1, showing a greater inhibition zone for the oregano oils treated bacteria as compared to the controls.

TABLE 1

| anti-bacterial effect of oregano oils | |
|---|---|
| The tested bacteria | Inhibition zone (mm) |
| E. coli | 15 |
| S. aureus | 19 |
| Salmonela | 21 |
| Clavibacter | 24 |
| Xanthomonas campestris | 22 |
| P. control | 8 |
| N, control | 0 |

Example 2: Preparation of Essential Oil Powder

Materials

For preparing the oil powder, the following materials were used:

Natural Oils:
Oregano oil 100% (essential oil) and Sesame oil 100% (carbon-base oil), both purchased from Makes Scents Natural SPA line, Lancaster Pa., USA.

Surfactants:
Thymol, Carvacrol, Tween80, Tween 65, Tween R85 and Egg Lecithin all purchased from Sigma-Aldrich.

Span 40 purchased from Fluka, Israel.

Zohar LQ-215 (Potassium fatty acids) and Zohar PT-50 (Potassium fatty acids) purchased from Zohar Dalia.

Silica Beads:
Tixosil ($SiO_2$) purchased from Rhodia group.

Aerosil 200 and Sipernat 50S ($SiO_2$, 20 μm) purchased from Evonik Industries AG.

Solvent:
Acetone and Acetonitrile purchased from J.T. Becker, Isopropanol (IPA), Gadot.

Methods

Powder Preparation

For laboratory scale production the powders containing the natural oils, surfactants and the silica beads were prepared using common lab glassware set up including laboratory bottles of 20-50 ml sizes, spatulas, magnetic stirrers and heating plates. Generally, the natural oil was weight and each was separately mixed with the selected surfactant in a 20 ml vial, to which the solvent was added. The mixtures of each oil were mixed and heated to a temperature of about 40 C until homogeneous solutions were obtained. To the homogenous solutions the silica beads were added until the liquid was absorbed by the beads. The bottles were left in the fuming hood overnight until all solvent has evaporated.

Loading of each of the oil in the final dry powders was 30-42%. The dry powders contained 2%-7% water.

All ratios of ingredients for powders preparation are provided in Tables 2A-2D.:

TABLE 2A

Oregano oil based powder

| Form. No. | Oregano oil | Surfactant | | | | | Silica beads | | Solvent |
| | | Tween 80 | Lecithin | Tween 85 | Tween 65 | Span 40 | Tixosil | Aerosil 200 | Acetone |
| --- | --- | --- | --- | --- | --- | --- | --- | --- | --- |
| ORG-18A | 0.5 g | 0.5 g | 0.1 g | | | | | 0.8 g | 1 g |
| ORG-18B | 0.5 g | 0.5 g | | | | 0.1 g | | 0.8 g | 1 g |
| ORG-18C | 0.5 g | 0.5 g | | 0.1 g | | | | 0.8 g | 1 g |
| ORG-18D | 0.5 gg | 0.5 g | | | 0.1 g | | | 0.8 g | 1 g |
| ORG-20C | 0.5 g | 0.5 g | | | 0.1 g | | 0.56 g | 0.24 g | 1 g |
| ORG-20D | 0.5 g | 0.5 g | | | 0.1 g | | 0.4 g | 0.4 g | 1 g |

TABLE 2B

Sesame oil based powder

| Form. No. | Sesame oil | Surfactant | | | | | Silica beads | | Solvent |
| | | Tween 80 | Lecithin | Tween 85 | Tween 65 | Span 40 | Tixosil | Aerosil 200 | Acetone |
| --- | --- | --- | --- | --- | --- | --- | --- | --- | --- |
| SES-19A | 0.5 g | 0.5 g | 0.1 g | | | | | 0.8 g | 1 g |
| SES-19B | 0.5 g | 0.5 g | | | | 0.1 g | | 0.8 g | 1 g |
| SES-19C | 0.5 g | 0.5 g | | 0.1 g | | | | 0.8 g | 1 g |
| SES-19D | 0.5 gg | 0.5 g | | | 0.1 g | | | 0.8 g | 1 g |
| ORG-21C | 0.5 g | 0.5 g | | | 0.1 g | | 0.56 g | 0.24 g | 1 g |
| ORG-21D | 0.5 g | 0.5 g | | | 0.1 g | | 0.4 g | 0.4 g | 1 g |

TABLE 2C

Self emulsified Oregano oil based powder using anionic surfactants

| Form. No. | Oregano oil | Surfactant | | Silica beads | | Solvent | |
| | | Zohar PT-50 | Zohar LQ 215 | Tixosil | Aerosil 200 | Isopropyl alcohol | Acetone |
| --- | --- | --- | --- | --- | --- | --- | --- |
| ORG-22A | 0.5 g | | 0.5 g | 0.56 g | 0.24 g | | 0 |
| ORG-22B | 0.5 g | | 0.5 g | 0.4 g | 0.4 g | | 1 g |
| ORG-24A | 0.5 g | | 0.25 g | 0.4 g | 0.4 g | | 0 |
| ORG-24B | 0.5 g | | 0.25 g | 0.4 g | 0.4 g | | 0.5 g |
| ORG-24C | 0.75 g | | 0.25 g | 0.4 g | 0.4 g | | 1 g |
| ORG-28 | 0.5 g | 0.25 g | | 0.56 | 0.24 g | 1 g | |

TABLE 2D

Self emulsified Sesame oil based powder using anionic surfactants

| Form. No. | Sesame oil | Surfactant | | Silica beads | | Solvent | |
| | | Zohar PT-50 | Zohar LQ 215 | Tixosil | Aerosil 200 | Isopropyl alcohol | Acetone |
| --- | --- | --- | --- | --- | --- | --- | --- |
| ORG-23A | 0.5 g | | 0.5 g | 0.56 g | 0.24 g | | 0 |
| ORG-23B | 0.5 g | | 0.5 g | 0.4 g | 0.4 g | | 1 g |
| ORG-25A | 0.5 g | | 0.25 g | 0.4 g | 0.4 g | | 0 |
| ORG-25B | 0.5 g | | 0.25 g | 0.4 g | 0.4 g | | 0.5 g |
| ORG-25C | 0.75 g | | 0.25 g | 0.4 g | 0.4 g | | 1 g |
| ORG-29 | 0.5 g | 0.25 g | | 0.56 | 0.24 g | 1 g | |

For greater amounts, laboratory electro-mechanical means similar to those used in the industry were employed. These included:

1. Vertical Mechanical Stirrer DC Hsiangtai equipped with propeller;
2. Peristaltic pump 4.4 Carter 4/6 cassette manostat and tubing;
3. Dynamic Exim 5 L powder mixer equipped with ribbon type mixing blades
4. Balances
5. Beakers 1-2 L and containers 1-3 L The preparation included weighting and mixing the oil with the surfactant(s) in a 1 L beaker, to which isopropyl alcohol was added while mixing until a homogenous solution was obtained. The silica beads (Sipernat 50S) were added to a 2 L beaker to which the homogenous solution was slowly (rate of 10 ml/min) added while mixing (30 rpm) until all liquid was absorbed into the beads.

All ratios of ingredients for powders preparation are provided in Tables 3A and 3B. The loading of the oil in the range of about 30%-42% was maintained.

TABLE 3A

Oregano oil based powder

| Form. No. | Oregano Oil | Surfactant Zohar PT 50 | Silica beads Sipernat 50S | Solvent IPA |
|---|---|---|---|---|
| 33 | 20 g | 10 g | 30 g | 20 g |
| 34 | 200 g | 100 g | 300 g | 200 g |
| 37A | 20 g | 15 g | 30 g | 20 g |
| 37B | 20 g | 10 g | 300 g | 15 g |
| 38 | 2 × 200 g | 2 × 125 g | 2 × 300 g | 2 × 125 g |

TABLE 3B

Sesame oil based powder

| Form. No. | Oregano Oil | Surfactant Zohar PT 50 | Silica beads Sipernat 50S | Solvent IPA |
|---|---|---|---|---|
| 35 | 200 g | 100 g | 300 g | 200 g |
| 39 | 200 g | 125 g | 300 g | 125 g |

In addition, also mixtures of powders (those containing Oregano oil and those containing Sesame oil) were prepared. Specifically, 400 g of formulation ORG-34 (beads carrying oregano oil) was mixed with 100 g of formulation SES-35 (beads carrying Sesame oil) in Dynamic Exim 5 L powder mixer at 10 rpm producing the mix O&S-A.

Each type of oil based powder was dried in the vacuum oven at 40 C for 24 hr prior to mixing the two populations together. [

In a different process, 800 g of formulation ORG-38 was mixed with 200 g of formulation SES-39 in Dynamic Exim 5 L powder mixer at 10 rpm producing the mixed beads formulation O&S-B.

The mixed bead powders were used as is.

Characterization

Determination of Water Content in Powder

Water content was determined using Mettler Toledo DL-38 Karl Fisher titrator according to USP <921> method.

Determination of Isopropanol Content in Powder

IPA content was determined using a headspace analysis according to the parameters bellow:

| | |
|---|---|
| Gas chromatograph | Agilent 7890 A |
| Column | BPX Volatiles, 60 m × 0.25 mm, 1.4 μm, SGE |
| Oven Program | 45° C. for 2 min, then 10° C./min to 100° C., then 25° C./min to 240° C., for 5 min. |
| Split | 1:25 |
| Mass spectrometer | Agilent 5975C |
| Autosampler program | CTC Combi PAL Pre-incubation time: 300 s Incubation temp.: 80° C. Syringe temp: 100° C. Volume of injection: 500 μl |
| Headspace vial | 20 ml |
| Volume of sample (water) | 2 ml |
| Calibration points (μg/ml) | 10, 25, 100, 500, 1000 |
| Concentration of ISTDs (ethanol) | 50 μg/ml |

Assay of Oregano Oil in Dry Powder Using HPLC

Impurities profile were determined in accordance with the method reported by H. Hajimehdipoor "A validated high performance liquid chromatography method for the analysis of thymol and carvacrol in *Thymus vulgaris* L. volatile oil" in Pharmacogn Mag. 2010 July-September; 6(23): 154 158 and adopted by SoluBest. For this purpose Nucleosil 100 C18 HD, 3μ, 150×3 mm column and Ultimate 3000 Dionex (Germany) HPLC system with photodiode array (PDA) detectors and Chromeleon Version 6.80 software packages were used. The mobile phase is Acetonitrile:Water (50:50, v/v). Minimum resolution between Carvacrol and Thymol peaks is 1.5.

Standard solutions were prepared in duplicate as following:

About 3 mg Thymol and 20 mg Carvacrol were weighted into 50 mL volumetric flask, and dissolved in 40 mL of diluents, then brought up to volume with the diluent and mixed. The resulting concentration of the Thymol standard solution was about 0.06 mg/mL and Carvacrol standard solution was about 0.4 mg/mL.

Sample solutions were prepared in duplicate as following:

About 70 mg of powdered sample was weighted into a 25 mL volumetric flask, then brought up to volume with the acetone and mixed.

Assay of Sesame Oil in Formulation Using GC

Sesame oil absorbed on silica beads was trans-methylated overnight with methanolic HCl solution at 60° C. Heptadecanoic acid, used as an internal standard, was added to beads before derivatization. Methyl esters of fatty acids were extracted with hexane and dried over anhydrous sodium sulfate prior to GC analysis.

Calibration standards were prepared from different concentrations of sesame oil and blank beads. Conditions of derivatization and amount of internal standard were the same as described in sample preparation.

Quantitative analysis of sesame oil in beads was performed using Agilent 7890 gas chromatograph equipped with FID detector. Compounds were separated on DB-23 capillary column.

Results

Conventional HPLC and GC analytical methods for Oregano and Sesame oils assay were employed.

The chromatograms of the tested powders showed that no degradation (according to the conventional markers, Thymol and Carvacrol aromatic compounds) of the oil was caused during the powder preparation and storage. Table 5 below provides % of Oregano oil and Sesame oil, respectively, in the powder based on Thymol and Carvacrol aromatic compounds analysis by HPLC.

TABLE 4

Oregano oil content in formulations as measured by HPLC

| Form. No | Sample | % via Thymol | % via Carvacrol |
|---|---|---|---|
| ORG-18A | ORG-18A-1 | 25.2 | 27.1 |
| | ORG-18A-2 | 27.1 | 28.3 |
| | Average | 26.1 | 27.7 |
| | Difference, % | 7.2 | 4.3 |
| ORG-28 | ORG-28-1 | 33.8 | 34.9 |
| | ORG-28-2 | 32.1 | 33.2 |
| | Average | 32.9 | 34.1 |
| | Difference | 5.5 | 5.2 |
| ORG-32 | ORG-32-1 | 28.0 | 30.3 |
| | ORG-32-2 | 28.1 | 30.7 |
| | Average | 28.0 | 30.5 |
| | Difference | 0.6 | 0.7 |
| ORG-34 | ORG-34-1 | 26.9 | 29.8 |
| | ORG-34-2 | 27.7 | 30.1 |
| | Average | 27.3 | 30.0 |
| | Difference | 2.1 | 2.0 |
| ORG-38 | ORG-38-1 | 28.8 | 28.7 |
| | ORG-38-2 | 28.0 | 29.3 |
| | Average | 28.4 | 29.0 |
| | Difference | 4.1 | 2.0 |

Table 5 provides the % of Sesame oil in the formulation as determined by GC Chromatograph.

TABLE 5

Sesame oil content in formulations as measured by GC chromatography

| Form. No. | Sample | % via C16:0 | % via C18:0 | % via C18:2 |
|---|---|---|---|---|
| SES-19A | SES-19A-1 | — | — | 28.0 |
| | SES-19A-2 | — | — | 27.6 |
| | Average | — | — | 27.8 |
| | Difference, % | — | — | 1.4 |
| SES-35 | SES-35-1 | 29.8 | 30.5 | 37.5 |
| | SES-35-2 | 30.6 | 30.6 | 33.4 |
| | Average | 30.2 | 30.6 | 35.5 |
| | Difference, % | 2.6 | 0.3 | 12.3 |
| SES-39 | SES-39-1 | 32.8 | 33.0 | 39.8 |
| | SES-30-2 | 31.5 | 32.3 | 37.4 |
| | Average | 32.2 | 32.7 | 38.6 |
| | Difference, % | 4.1 | 2.2 | 6.4 |

The water content measured using Karl Fisher titration found that the powder contains 5-7% of water. It appears the source of the water is from Zohar PT 50 surfactant, which contents 50% of water.

As to IPA content, GC Headspace precise analysis demonstrate the IPA content in the formulations, which is summarized in Table 6.

TABLE 6

IPA content in the powders

| Form. No | Sample Amount (gr.) | IPA (µg/ml) | IPA (%) |
|---|---|---|---|
| 34 | 19.6 | 1.265 | 12.9 |
| 35 | 200 | 1.139 | 11.4 |
| 38 | 20.3 | 1.117 | 11.0 |
| 39 | 19.8 | 492 | 5.0 |

As can be seen from the Table 6, the amount of IPA varies from 5 to 13%. However, in the field, the formulations were diluted for at least 30 times and as such, the content of IPA was reduced to 0.17-0.43%, which is negligible and very safe amount.

The different types of dry powders prepared showed stable after long term (more than a year) storage. In addition to the above, it is noted that the powders have a characteristic odor. The oregano oil based formulations have off-white color and sesame oil based powders are white.

Upon contact with water tested formulations (ORG-28 and SES-29 immediately form an emulsion, which were stable for 24 h. The emulsions consisted of the droplets of 3-10 microns. The spray-ability of the emulsions was good without clogging the filters.

Safety studies in the field showed that the tested oil based powders were safe. This was determined by the presence (or not) of burns on the plants, as determined by conventional phytotoxicty parameters.

Further, long term (8 weeks) stability of the powders was determined. Specifically, the Oregano and Sesame based powders were separately sealed in aluminum foil bags and placed at accelerating storing conditions (40° C. for 8 weeks). Assay of Oregano oil was measured via two major constituents—Carvacrol and Thymol—in the beginning of the stability study (initial point) and after 8 weeks using HPLC-UV technique. The obtained values were normalized to the amounts of markers in the pure oregano oil.

Assay of sesame oil was measured via two major constituents—C16:0 and C18:0—in the beginning of the stability study (initial point) and after 8 weeks using GC-FID analysis of methylated fatty acids. Trans methylation was performed upon acidic catalysis (with MeOH/HCl) using C17:0 as an internal standard. The obtained values were normalized to the amounts of markers in the pure sesame oil.

No significant changes were observed in the both formulations: amount of oregano and sesame oils were similar before and after stability studies.

Water content was tested using Karl Fisher method. The amount of water was reduced on 42% after 8 weeks of storing in accelerating conditions in both formulations.

Isopropanol content was tested using GC method. The amount of IPA was reduced on 36% after 8 weeks of storing in accelerating conditions in oregano formulation, but it was preserved in the sesame formulation.

Without being bound by theory, it appears that the containers were leaky and in order to reduce water or IPA loss, the containers may be more hermetically sealed.

Powders stored 8 weeks at 40 C showed good ability to form a stable emulsion similar to those of the initial powders. The stability measurements are summarized in Table 7 below:

TABLE 7

| | | Stability Assays | | | | |
|---|---|---|---|---|---|---|
| | Time point | Oregano oil (%) | | Sesame oil (%) | | |
| | | via C16:0 | via C18:0 | via Thymol | via Carvacrol | Water, % | IPA, % |
| Oregano powder SORG-121-38 | Initial | | | 28.4 | 29.0 | 7.05 | 11 |
| | 8 weeks | | | 29.8 | 29.1 | 4.05 | 7 |
| Sesame powder SES-121-39 | Initial | 32.2 | 32.7 | | | 6.65 | 5 |
| | 8 weeks | 33.3 | 34.2 | | | 3.81 | 5 |

Example 3: Solubilization and Anti-Bacterial Activity with Different Surfactants In order to create stable oil-in-water emulsion a surfactant (emulsifying agent) with HLB of 8-20 is required. Thus, in the following, two surfactants were tested Tween 80 having an HLB value of 15 and potassium salt of fatty acids extracted from palm, coconut, olive, castor and cottonseed plants (potassium salt oleate having an HLB value of 20).

It has been found that with the potassium salts of fatty acids the ratio of oil/surfactant required for obtaining a stable emulsion of oregano oils is 1:0.4 while with Tween 80, the required oil/surfactant ratio was 1:1.

The correlation between HLB values and solubilization capacity of each surfactant was found in the current case of Oregano oil, i.e. better solubilization with potassium salts of fatty acids. Isopropanol was used as process aid compound, which also provided additional stability for producing emulsions.

For anti-bacterial effect, several emulsifiers were tested with oregano oil and sesame oil, in water.

The tested emulsifiers included: Tween 20; Tween 80; Triton X 100; Lecithin; SDS; Sodium Stearate and Potassium fatty acid. Each emulsifiers was tested at the following concentrations (in percentage) 1; 5; 10; 15; 20 for a mixture of water containing 25% oregano oil with 5% sesame oil.

The stability during the first 24 hours (i.e. lack of phase separation) and anti-bacterial activity of each emulsion were determined. Anti bacterial activity was determined by measuring the inhibition zones of 20 l emulsion towards the following plant pathogenic bacteria: *Clavi bacter; Xanthomonas* and *Streptomyces* spp. and by spraying the emulsions on pepper plants as test plants for phytotoxicity symptoms.

The results showed that potassium fatty acid was the most suitable material in creating stable emulsion at 10% concentration; the inhibition zone of the potassium salt of fatty acid was greater than the other tested emulsions and had no phytotoxicity on pepper plants. The data obtained (not shown) clearly demonstrated phytotoxicity on pepper plants when the emulsifiers were Tween 20 Tween 80, Triton X100 or SDS, as the plants sprayed with the emulsions created therewith died, while being very vital when sprayed with the sodium stearate potassium fatty acid.

In a different set of experiments, the oregano oil and surfactant were absorbed on silica beads (with the air of isopropanol, as described above). Good anti-bacterial results were obtained when 0.5% of oregano-based powder was dispersed in water. This powder contained about 25% of oregano oil and 10% of potassium fatty acids emulsifier, namely, a concentration of 0.125% oregano oil in emulsion was active enough and needed only 0.05% of surfactant to be solubilized from the powder form.

Surprisingly, even a lower concentration of powder was sufficient to produce good crop protection in a greenhouse study. Only 0.2% of powder and consequently 0.05% of oregano oil was enough to disperse in water (to form an emulsion) and showed excellent and repeatable anti-bacterial effect with the plants being treated therewith remaining completely vital as compared to infected, but untreated control.

Example 4: Preferred Formulation and Powder Preparation

Materials and Compositions

Oils: Sesame oil 100% (SPAline Lot sicP1A11/01); Oregano oil 100% (SPAline Lot 0015181)

Surfactant: Zohar PT-50 (Zohar Dalia, Batch 05511PM1142);

$SiO_2$ particles: Sipernet 50S (20 m, Evonik Industries, lot 1462)

Alcohol: Isopropanol (IPA, Gadot).

Formulation:

| Amount | Oregano oil | Sesame oil | Zohar PT-50 | Sipernat 50S | IPA | Total |
|---|---|---|---|---|---|---|
| Kg | 40 | 10 | 31 | 75 | 21 | 177 |
| % | 22.6 | 5.6 | 17.5 | 42.4 | 11.9 | 100 |

Preparation of Powder

First, the oregano oil and sesame oil were mixed, to which IPA was added until a homogenous solution was obtained. To the solution, the surfactant was added by mixing until a non-viscous homogenous solution was obtained. The solution was sprayed on the $SiO_2$ powder and mixing was peformed using low sheer force equipment until all liquid was absorbed and continued for an additional period of 15-30 min. Then the powder was grind to breakdown aggregates and sieved through mesh 1,000 m. For storage, the bag containing the powder was hermetically sealed and stored. Storage was for at least 2 years, at 15-30 C.

The invention claimed is:

1. An agricultural composition comprising particulate matter, the particulate matter comprising:

porous particles comprising silica dioxide ($SiO_2$) particles, the porous particles having a size distribution in the range of 15 μm to 22 μm and carrying at least one natural oil and at least one surfactant at least partially absorbed within pores of the porous particles, the at least one natural oil comprising at least one agriculturally effective fungicidal or pesticidal essential oil, each of the particles holding between 25% to 50% w/w natural oil out of the total weight of the particulate matter, wherein the particulate matter is in the form of an essentially dry powder, and wherein, upon contacting the particulate matter with water, an agriculturally effective anti-microbial oil-in-water emulsion is formed.

2. The particulate matter of claim 1, wherein the surfactant is in an amount of between 5 to 10% w/w surfactant out of the total weight of the particulate matter.

3. The particulate matter of claim 1, wherein the particles are silica dioxide (SiO$_2$) particles.

4. The particulate matter of claim 1, wherein each particle has a surface area in the range of 400-550 m$^2$/g or each particle has an oil capacity in the range of 250-350 ml/100 gram particles.

5. The particulate matter of claim 1, wherein the at least one essential oil comprises Oregano oil.

6. The particulate matter of claim 1, wherein the at least one natural oil further comprises at least one carbon rich oil.

7. The particulate matter of claim 6, wherein the ratio of the at least one essential oil and the at least one carbon-rich nutrient oil is in the range of 60:40 and 100:0.

8. The particulate matter of claim 6, wherein the at least one essential oil comprises Oregano oil and wherein the at least one carbon-rich nutrient oil comprises Sesame oil.

9. The particulate matter of claim 1, wherein the particulate matter has a water content of no more than 10% w/w out of the total weight of the particulate matter.

10. The particulate matter of claim 1, wherein the particulate matter has up to 5% w/w organic solvent.

11. A composition comprising a particulate matter of claim 1.

12. The composition of claim 11, wherein the at least one natural oil is at least two natural oils carried on the same particle.

13. The particulate matter of claim 1, wherein the particles are selected from the group consisting of silica dioxide particles, latex beads, calcium carbonate sorbent particles, cellulose beads, polystyrene adsorbents beads, charcoal, sepharose beads, emulsan-alginate beads, chitosan beads, sodium alginate beads, styrene-maleic acid copolymer beads, styrene-divinylbenzene beads, and cellulose paper beads, or any combinations thereof.

14. The particulate matter of claim 1, wherein the at least one essential oil is derived from *Origanum vulgare*, *Origanum* spp., *Mentha* spp., *Thymus* spp., *Myrtus* spp., *Ocimun* spp., *Lavandula* spp., *Micromeria* spp., *Coriandum* spp., *Aloysia* spp., *Melissa* spp., *Salvia* spp., *Petoselinum* spp., *Rosmarinus* spp., *Prunella* spp., or *Cuminum* spp., or any combinations thereof.

15. The particular matter of claim 1, wherein the particles hold between 25% to 35% w/w natural oil out of the total weight of the particulate matter.

16. The particular matter of claim 1, wherein the particles hold between 28% to 32% w/w natural oil out of the total weight of the particulate matter.

17. A composition comprising particulate matter, the particulate matter comprising:
porous particles comprising silica dioxide (SiO2) particles, the porous particles having a size distribution in the range of 15 μm to 22 μm and carrying at least one natural oil and at least one surfactant comprising a potassium salt of a fatty acid at least partially absorbed within pores of the porous particles, the at least one natural oil comprising at least one agriculturally effective fungicidal or pesticidal essential oil, each of the particles holding between 25% to 50% w/w natural oil out of the total weight of the particulate matter,
wherein the particulate matter is in the form of an essentially dry powder,
wherein the at least one agriculturally effective fungicidal or pesticidal essential oil is derived from a plant selected from the group consisting of derived from *Origanum* spp., *Mentha* spp., *Thymus* spp., *Myrtus* spp., *Ocimun* spp., *Lavandula* spp., *Micromeria* spp., *Coriandum* spp., *Aloysia* spp., *Melissa* spp., *Salvia* spp., *Petoselinum* spp., *Rosmarinus* spp., *Prunella* spp., or *Cuminum* spp., or any combinations thereof, and
wherein, upon contacting the particulate matter with water, an agriculturally effective anti-microbial oil-in-water emulsion is formed.

\* \* \* \* \*